United States Patent [19]

Rollins et al.

[11] Patent Number: 5,459,128
[45] Date of Patent: Oct. 17, 1995

[54] HUMAN MONOCYTE CHEMOATTRACTANT PROTEIN-1 (MCP-1) DERIVATIVES

[75] Inventors: Barrett Rollins; Yu J. Zhang, both of Brookline, Mass.

[73] Assignee: Dana-Farber Cancer Institute, Boston, Mass.

[21] Appl. No.: 330,218

[22] Filed: Oct. 27, 1994

Related U.S. Application Data

[63] Continuation-in-part of Ser. No. 152,301, Nov. 12, 1993, abandoned.

[51] Int. Cl.⁶ .......................... C07K 14/52; C08H 1/00; A61K 38/19; A61K 45/05
[52] U.S. Cl. .......................... 514/8; 514/12; 514/21; 530/351; 530/395; 530/402; 530/409; 424/85.1
[58] Field of Search .......................... 530/350, 351, 530/395, 402, 409; 514/8, 12, 21; 424/85.1; 930/140, 141

[56] References Cited

U.S. PATENT DOCUMENTS

| | | | |
|---|---|---|---|
| 5,212,073 | 5/1993 | Rollins et al. | 435/69.5 |
| 5,288,711 | 2/1994 | Mitchell et al. | 514/56 |

OTHER PUBLICATIONS

Koch, A. E. et al., "Enhanced Production of the Chemotactic Cytokines Interleukin-8 & Monocyte Chemoaltiactant Protein-1 in Human Aortic Aneurysms", Am. J. Pathol., 142(5), 1423-1431, May 1993.
Rollins, Barrett J. et al., "The Human Homolog of the JE Gene Encodes a Monocyte Secretory Protein", Molecular and Cellular Biology, 9(11):4687-4695, (1989).
Rollins, Barrett J. et al., "Recombinant Human MCP-1/JE Induces Chemotaxis, Calcium Flux, and the Respiratory Burst in Human Monocytes", Blood, 78(4):1112-1116, (1991).
Prickett, Biotechniques, 7:580-589, (1989).
Gronenborn, A. M. and Clore, G. M., "Modeling the three-dimensional structure of the monocyte chemo-attractant and activating protein MCAF/MCP-1 on the basis of the solution structure of interleukiin-8", Protein Eng., 4:263-269 (1991).
Beall, C. J., Mahajan, S. and Kolattukudy, P. E., "Conversion of monocyte chemoattractant protein-1 into a neutrophil attractant by substitution of two amino acids", J. Biol. Chem., 267:3455-3459 (1992).

Primary Examiner—William H. Beisner
Assistant Examiner—Nancy J. Degen
Attorney, Agent, or Firm—Hamilton, Brook, Smith & Reynolds

[57] ABSTRACT

The invention relates to a human MCP-1 derivative, and pharmaceutical compositions thereof, wherein human MCP-1 has been modified such that the protein inhibits monocyte chemoattractant activity. Successful inhibition of the activity is found where the MCP-1 is modified in one or more of the following: a) the 28-tyrosine is substituted by aspartate, b) the 24-arginine is substituted by phenylalanine, c) the 3-aspartate is substituted by alanine, and/or d) the 2–8 amino acid sequence is deleted. The claimed MCP-1 derivatives can be administered to a patient in need of inhibiting MCP-1 monocyte chemoattractant activity. For example, the derivatives can be used to prevent restenosis, such as that which is common in a patient undergoing coronary artery angioplasty. The invention further relates to compositions and methods of inhibiting monocyte chemoattractant activity of MCP-1 employing the derivatives described.

27 Claims, 3 Drawing Sheets

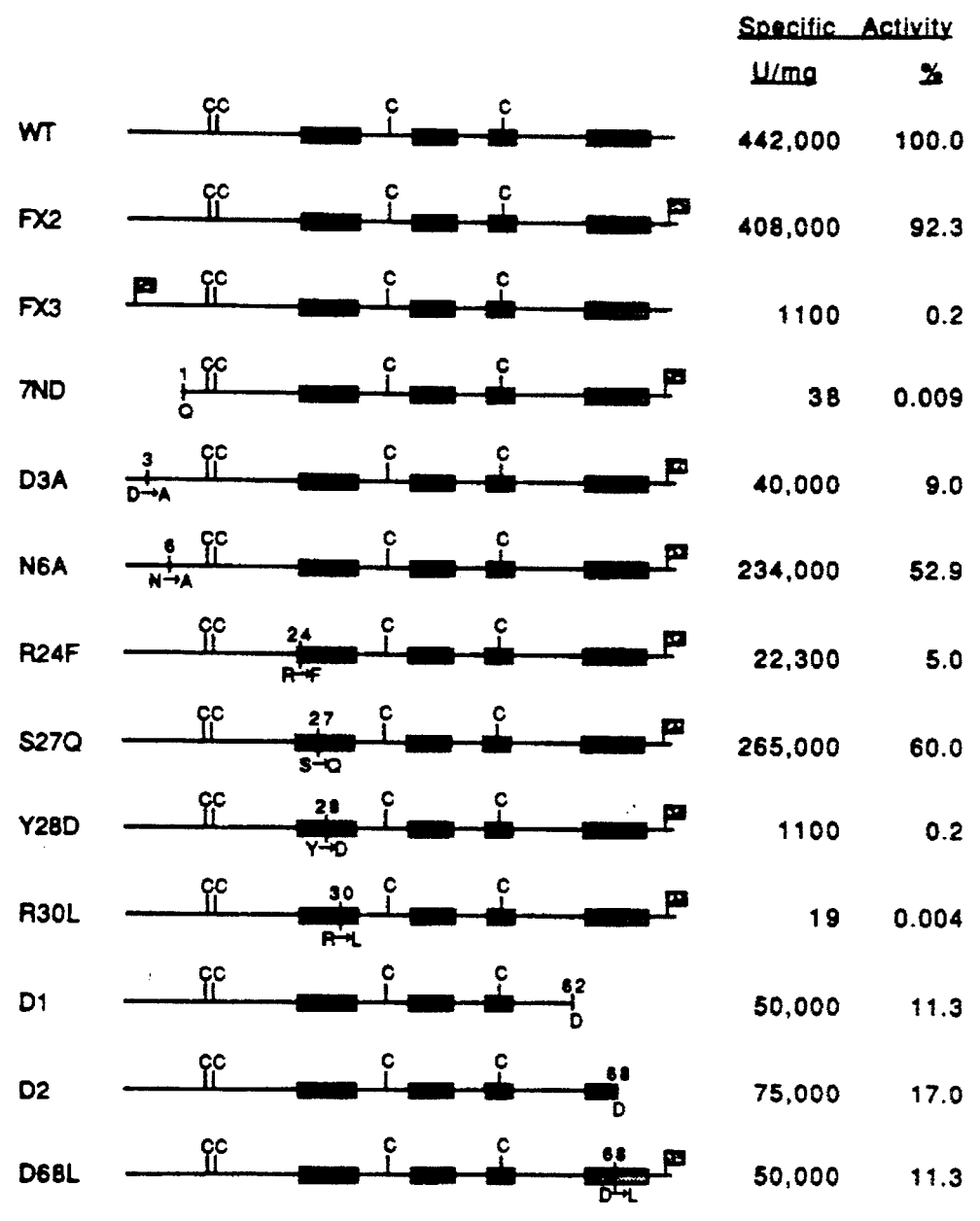

| | | Specific Activity | |
|---|---|---|---|
| | | U/mg | % |
| WT | | 442,000 | 100.0 |
| FX2 | | 408,000 | 92.3 |
| FX3 | | 1100 | 0.2 |
| 7ND | | 38 | 0.009 |
| D3A | | 40,000 | 9.0 |
| N6A | | 234,000 | 52.9 |
| R24F | | 22,300 | 5.0 |
| S27Q | | 265,000 | 60.0 |
| Y28D | | 1100 | 0.2 |
| R30L | | 19 | 0.004 |
| D1 | | 50,000 | 11.3 |
| D2 | | 75,000 | 17.0 |
| D68L | | 50,000 | 11.3 |

FIGURE 2

HUMAN MONOCYTE CHEMOATTRACTANT PROTEIN-1 (MCP-1) DERIVATIVES

GOVERNMENT SUPPORT

The invention described herein was supported in whole or in part by grants from the National Institutes of Health.

RELATED APPLICATION

This application is a continuation-in-part of application Ser. No. 08/152,301 filed on Nov. 12, 1993, now abandoned, which is incorporated herein by reference in its entirety.

BACKGROUND

Chemokines are proinflammatory cytokines that are chemoattractants and activators of specific types of leukocytes. Members of this family share common structural motifs, in particular the positions of four cysteines, as well as other highly conserved regions of primary structure. Despite their similarities, most chemokines have non-overlapping target cell specificities. Chemokines can be grouped into two subfamilies, chemokine-α and chemokine-β proteins, based on structural and genetic criteria.

Monocyte chemoattractant protein-1 (MCP-1) is a member of the chemokine-β family of proinflammatory cytokines. The amino acid sequence of human MCP-1 is disclosed in Rollins, Molecular and Cellular Biology, Vol. 9, No. 11, pp. 4687–4695, Nov. 1989. MCP-1 attracts and activates monocytes, to the exclusion of neutrophils, at subnanomolar concentrations. MCP-1 is structurally and genetically related to interleukin-8 (IL-8), a neutrophil-specific chemo-attractant, which is member of the chemokine-α family.

Monocytes are attracted to damaged coronary arteries, such as the damage caused by coronary artery angioplasty, and are involved in causing restenosis.

SUMMARY OF THE INVENTION

The invention relates to MCP-1 derivatives mutated such that said derivatives inhibit the monocyte chemoattractant activity of endogenous MCP-1, preferably human MCP-1, and pharmaceutical compositions thereof. In a preferred embodiment, the MCP-1 derivative has been modified at the 28-tyrosine, the 24-arginine, the 3-aspartate and/or in amino acids between about 2 and about 8. In one embodiment, the mutation is not at the 28-tyrosine. Preferably, the MCP-1 derivative is not substituted at the 28-tyrosine by leucine and/or substituted at the 30-arginine by valine. Successful inhibition of the activity is found where the MCP-1 is modified in one or more of the following ways: a) the 28-tyrosine is substituted by aspartate, b) the 24-arginine is substituted by phenylalanine, c) the 3-aspartate is substituted by alanine, and/or d) the 2–8 amino acid sequence is deleted.

The claimed MCP-1 derivatives can be administered to a patient in need of inhibiting MCP-1 monocyte chemoattractant activity. Advantageously, the derivatives can be used to prevent restenosis, such as that which is typical in many patients undergoing coronary artery angioplasty.

The above and other features of the invention will now be more particularly described and pointed out in the claims. It will be understood that the particular derivatives embodying the invention are shown by way of illustration and not as a limitation of the invention. The principles and features of this invention may be employed in varied and numerous embodiments without departing from the scope of the invention.

BRIEF DESCRIPTION OF THE DRAWINGS

FIG. 2 is a chart of the mutations prepared and the specific chemotaxis activity of the mutants.

DETAILED DESCRIPTION OF THE INVENTION

Figure 1:
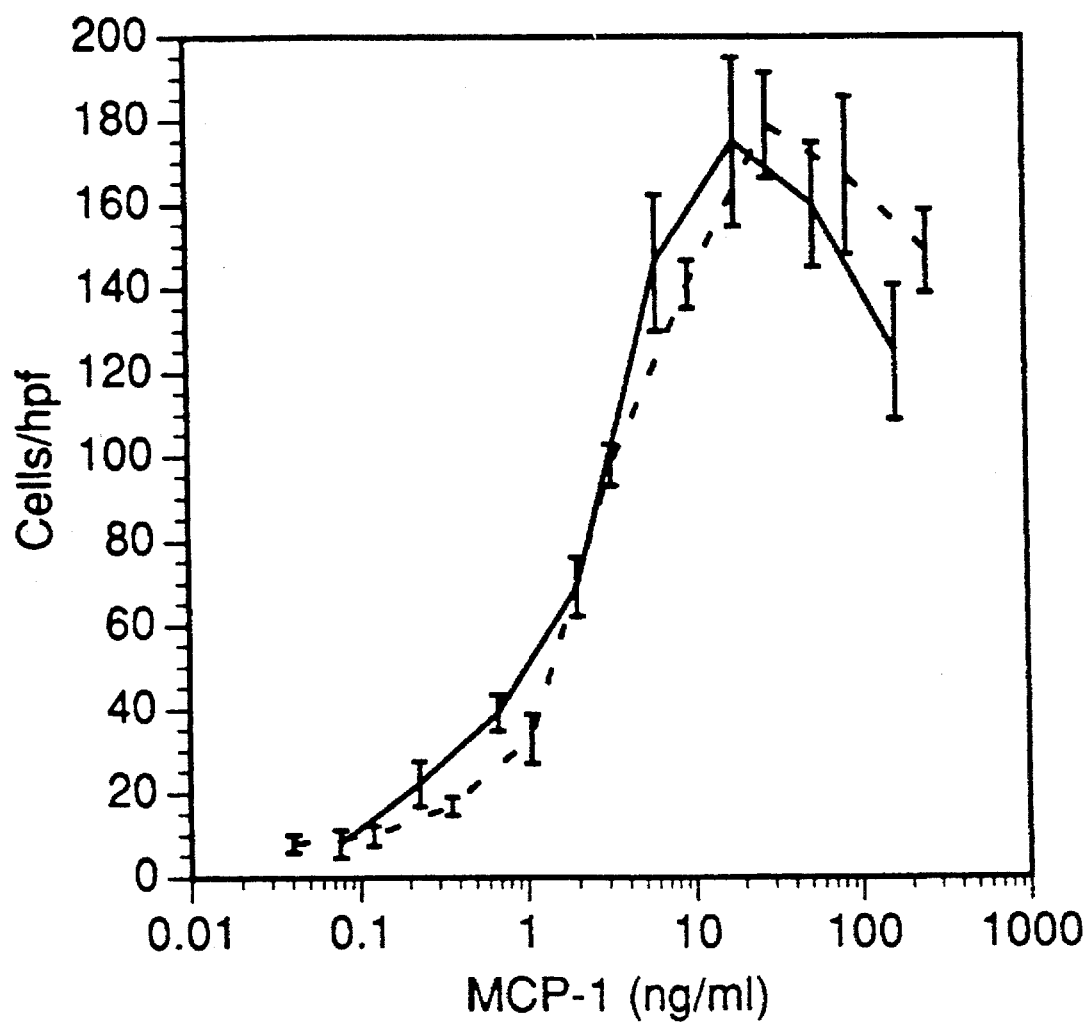
FIG. 1 is a response curve of wild type MCP-1 and FLAG epitope tagged MCP-1 proteins.
Figure 3:
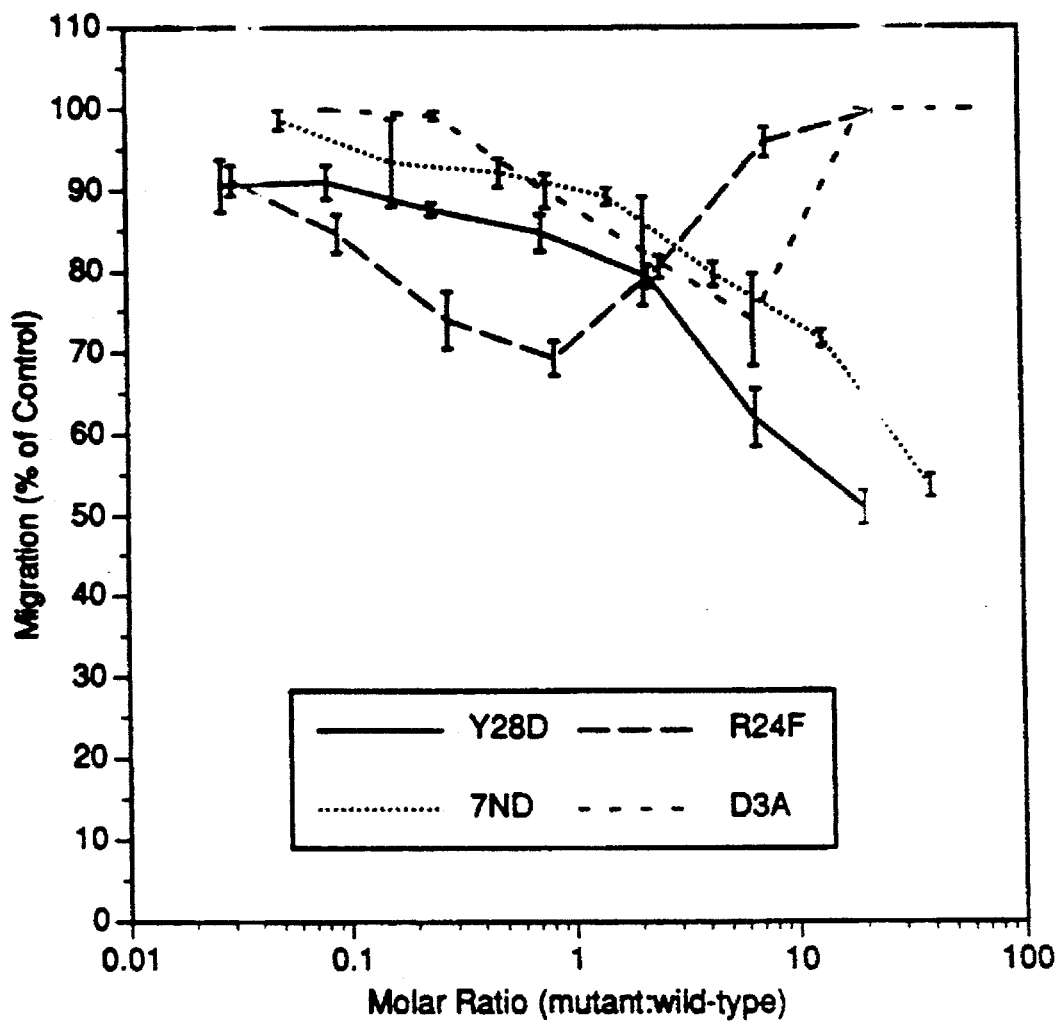
FIG. 3 is a dose response curve for MCP-1 inhibition of four of the claimed embodiments.

The present invention is based on the finding that regions of MCP-1 can be mutated to inhibit endogenous MCP-1 monocyte chemoattractant activity. Mutants of MCP-1 were developed that possessed the desired inhibitory activity. Successful inhibition of the activity is found, for example, where the human MCP-1 is modified in one or more of the following: a) the 28-tyrosine is substituted by aspartate, b) the 24-arginine is substituted by phenylalanine, c) the 3-aspartate is substituted by alanine, and/or d) the 2–8 amino acid sequence is deleted. Specific mutants where only one modification set forth above was accomplished were designated Y28D, R24F, D3A, and 7ND, respectively.

Mutation of human MCP-1 other than the point mutations given above are also envisioned within this invention. It is further possible to develop MCP-1 mutants derived from other mammals possessing a monocyte chemoattractant protein which will inhibit endogenous MCP-1. Employing the techniques described herein for the development of mutant proteins and screening the mutants developed, other equivalent mutant proteins can be identified and isolated.

The term "derivative" as employed herein, is defined as encompassing the whole protein, any active portion thereof or any addition product of the parent protein.

The derivatives of the claimed invention can be made according to known methods in the art, including the polymerase chain reaction. The polymerase chain reaction can be used to create point mutations in the cDNA for human MCP-1. R. Higuchi, "Recombinant PCR" *PCR Protocols: A Guide to Methods and Applications*, editors Innis, M. A.; Gelfand, D. H.; Sninsky, J. J.; and White, T. J., Academic Press, N.Y. 1990, incorporated herein by reference. cDNA'S can be transiently transfected into an appropriate expression system to produce mutant proteins. Appropriate expression systems which can be used include prokaryote and eukaryotes. To avoid problems of inducing proper folding of bacterially induced proteins, the protein is preferably expressed in COS cells.

By way of example, construction of epitope-tagged MCP-1 and MCP-1 mutations can be prepared employing the polymerase chain reaction. Any suitable source of the cDNA for MCP-1 in any suitable cloning vector can be employed as a template. A preferred cloning vector which can be employed is pGEM-hJE34 (human MCP-1 cDNA in pGEM-7 (Promega, Wis.)). In one embodiment, recombinant PCR was used to insert 30 nucleotides immediately 5' to the termination codon (position 366) encoding the FLAG epitope (Prickett, Biotechniques, 7, pp 580–589, (1989)) with a two glycine spacer.

The cDNA so obtained were cloned into a suitable expression vector, pmt21 (Genetics Institute), to yield a plasmid designated pFX2.

Similar techniques were used to insert the FLAG epitope and spacer immediately 3' to the codon for aspartate-3 in processed MCP-1 (nucleotide position 146); this expression plasmid was designated pFX3. With pFX2 as template, recombinant PCR was used to insert termination codons or single amino acid changes, as desired.

The cDNA so obtained was cloned into a suitable expression vector, such as pmt21 (Genetics Institute), to yield a suitable plasmid.

Expression of MCP-1 and its derivatives can be accomplished by known techniques. A wide variety of expression vehicles can be used. One preferred expression vehicle is the COS cell line. Expression of the protein can be determined and quantified by routine methods in the art, such as immunoblotting and laser densitometry.

As set forth above, MCP-1 attracts and activates monocytes. Monocytes are attracted to damaged coronary arteries, such as the damage caused by coronary artery angioplasty, and are involved in causing restenosis. Administration of inhibitors to the recruitment of monocytes will be useful in preventing restenosis, rheumatoid arthritis, chronic pulmonary inflammation and other conditions linked to the recruitment of monocytes.

The derivatives of the claimed invention can be administered alone or in a suitable pharmaceutical composition. Modes of administration are those known in the art, such as parenteral application.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

It will be appreciated that the actual amounts of the MCP-1 derivative in a specific case will vary according to the specific compound being utilized, the particular composition formulated, the mode of administration and the age, weight and condition of the patient, for example. Dosages for a particular patient can be determined by one of ordinary skill in the art using conventional considerations, (e.g. by means of an appropriate, conventional pharmacological protocol).

The invention is further specifically illustrated by the following examples.

EXEMPLIFICATION

Construction and expression of epitope-tagged MCP-1 and wild-type MCP-1:

Starting with pGEM-hJE34 (human MCP-1 cDNA in pGEM-7 (Promega, Wis.)) as a template, recombinant PCR was used to insert 30 nucleotides immediately 5' to the termination codon (position 366) encoding the FLAG epitope (Prickett, (1989)) with a two glycine spacer. Sequence analysis of the resulting cDNA revealed no other base alterations, and the entire cDNA was cloned into the expression vector pmt21 (Genetics Institute) to yield a plasmid designated pFX2.

COS cells were suspended in serum-free Dulbecco's modified Eagle's medium (DMEM) at $5 \times 10^6$ cells/ml. Four $\times 10^6$ cells (0.8 ml) were placed in an electroporation cuvette with a 0.4 cm gap, 10 μg plasmid DNA was added, and the cells were electroporated at 0.28 kV, 960 μF (yielding a time constant of 10–13 msec). Cells were allowed to recover in the cuvette at room temperature for 10 minutes, then plated in two 100 mm dishes in DMEM with 10% bovine calf serum. After 24 hours, medium was changed to serum-free DMEM. After an additional 24 hours, conditioned medium was collected, cells and debris were removed by centrifugation, and the medium was stored at −70° C.

Wild-type MCP-1 was also produced by COS cell transfection, as described above.

Construction and expression of MCP-1 mutations:

Similar techniques as described by Higuchi, above, were used to insert the FLAG epitope and spacer immediately 3' to the codon for aspartate-3 in processed MCP-1 (nucleotide position 146); this expression plasmid was designated pFX3. Based on modeling considerations as well as structure/activity data from other chemokines (in particular IL-8), MCP-1 mutations in three regions were constructed: namely the N-terminus, the first inter-cysteine loop, and the C-terminal predicted α-helix (FIGS. 2 and 4). With pFX2 as template, recombinant PCR was used to insert termination codons or single amino acid changes. All mutations were confirmed by sequence analysis of both DNA strands.

Immunoblotting:

Conditioned medium from transfected COS cells was boiled in sample buffer and subjected to electrophoresis through a 15% polyacrylamide gel in SDS. In some cases, medium was first concentrated using a Centricon-10 device (Amicon, Danvers, Mass.).

Proteins were electrophoretically transferred to nitrocellulose and probed either with an anti-FLAG M1 monoclonal antibody (International Biotechnologies, Inc., New Haven, Conn.) or with rabbit anti-MCP-1 antiserum.

Blots were developed using the appropriate horseradish peroxidase-conjugated secondary antibody and substrate solution (Vector Laboratories, Burlingame, Calif.).

Quantitation of MCP-1 and its derivatives:

MCP-1 was expressed as a FLAG fusion protein in *E. coli* using the FLAG Biosystem and purified using an anti-FLAG affinity column (International Biotechnologies, Inc., New Haven, Conn.). Known amounts of pure FLAG-MCP-1 fusion protein were included in every immunoblot for MCP-1 produced by COS cells. Immunoblots were then analyzed by laser densitometry (Pharmacia, Piscataway, N.J.) and the mass of each COS cell-produced protein was determined by reference to the FLAG-MCP-1 fusion standard. The amount of COS cell supernatant loaded in each well generated an immunoblot signal within the linear response range of the laser densitometer. When possible, samples were quantitated using both anti-FLAG and anti-MCP-1 antibodies. There were no disparities between amounts of protein determined with the two antibodies except when one of the epitopes was absent.

Monocyte chemotaxis assay:

Human peripheral blood mononuclear cells were prepared from volunteers as described (Rollins, Blood, 78, pp 1112–1116 (1989)). Chemotaxis assays were performed using a multiwell chamber fitted with a polycarbonate filter having 5μ pores as described. Each COS cell supernatant was tested over a wide range of dilutions, and the concentration of monocyte chemoattractant activity (MCA) in each supernatant was defined as the inverse of the dilution giving half-maximal chemotactic response.

Wild-type MCP-1 and FX2 had similar dose response characteristics, FIG. 1. Using the quantitation results from immunoblotting, analysis of the dose response curves showed that the specific activity of FX2 is 408,000 U/ml while that of wild-type MCP-1 is 442,000 U/ml. Both values compared favorably with the specific activity determined for purified, eukaryotically-produced, recombinant MCP-1, suggesting that the epitope tag does not interfere with MCP-1's ability to attract monocytes in vivo.

Each of the mutations constructed, illustrated in FIG. 2, were tested for monocyte chemotaxis activity in the same manner. As set forth above, the mutations were constructed in three regions, the N-terminus, the first inter-cysteine loop, and the C-terminus. At the N-terminus, insertion of the FLAG epitope immediately after the N-terminal glutamine destroyed the protein's monocyte chemoattractant activity (FX3). Consistent with that finding was the fact that deletion of amino acids 2-8 also yielded an inactive protein. In an attempt to accomplish finer mapping, the two charged amino acids were changed in this region (aspartate-3 and asparagine-6) to alanine. Changing aspartate-3 significantly reduced the activity of the protein, while changing asparagine-6 yielded a protein that retained 52.9% of wild-type MCP-1's activity.

Next, four point mutations in the first intercysteine loop were constructed. Mutations of arginine-24 to phenylalanine, tyrosine-28 to aspartate, and arginine-30 to leucine all produced proteins with activities that were only a fraction of wild-type. However, mutation of another polar amino acid in the same region, namely serine-27, produced a protein with 60% of the activity of wild-type.

Finally, manipulations of the C-terminal α-helix produced proteins that were still able to signal, but had reduced potency compared to wild-type. Deletions of half (D2) or all (D1) of the α-helix yielded proteins with 17% and 11.3% of wild-type activity, respectively. In the predicted model structure of dimeric MCP-1, aspartate-68 projects into a predicted receptor binding cleft between two α-helices. Mutation of this amino acid to leucine had the same effect as deletion of the entire helix.

Competition for biological effects:

Mutated MCP-1 derivatives were tested for their ability to inhibit monocyte chemotaxis in vitro in response to non-mutated MCP-1. To a fixed concentration of FX2, increasing amounts of medium conditioned by COS cells expressing mutant proteins were added. Only Y28D, R24F, 7ND, and D3A demonstrated an ability to inhibit wild type MCP-1. FIG. 3 shows that Y28D and 7ND were able to inhibit monocyte chemotaxis to FX2 by approximately 50% at the highest ratios tested. (The upper limit was dictated by the concentration of mutation protein in conditioned medium.) Y28D was slightly more effective than 7ND on a molar basis with an $ID_{50}$ corresponding to ≈300 ng/ml in the presence of 10 ng/ml wild-type MCP-1. R24F reduced MCP-1's chemoattractant effect to 69% of control at a molar ratio of 1:1. Although R24F itself had monocyte chemoattractant activity of only 5% of wild-type, addition of more R24F beyond a 1:1 molar ratio with wild-type led to increasing chemoattractant activity. D3A reduced MCP-1's activity to 80% of control at a molar ratio of 10:1, but since it also has chemoattractant activity, higher molar ratios showed loss of inhibition. Inhibitory activity was specific for MCP-1 since the mutations did not inhibit monocyte chemotaxis in response to formyl-methionyl-leucyl-phenylalanine (fMLP).

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A Monocyte Chemoattractant Protein-1 (MCP-1) derivative capable of inhibiting the monocyte chemoattractant activity of endogenous MCP-1, with the proviso that the derivative has not been modified by the substitution of 28-tyrosine by leucine and/or the substitution of 30-arginine by valine.

2. A human Monocyte Chemoattractant Protein-1 (MCP-1) derivative wherein human MCP-1 has been modified in one or more of the following ways:

a) the 28-tyrosine is substituted by aspartate;

b) the 24-arginine is substituted by phenylalanine;

c) the 3-aspartate is substituted by alanine; and/or d) the 2–8 amino acid sequence is deleted.

3. A human Monocyte Chemoattractant Protein-1 (MCP-1) derivative wherein the 2–8 -tyrosine of human MCP-1 is substituted by aspartate.

4. A human Monocyte Chemoattractant Protein-1 (MCP-1) derivative wherein the 2–8 amino acid sequence of human MCP-1 is deleted.

5. A human Monocyte Chemoattractant Protein-1 (MCP-1) derivative wherein the 24-arginine of human MCP-1 is substituted by phenylalanine.

6. A human Monocyte Chemoattractant Protein-1 (MCP-1) derivative wherein the 3-aspartate of human MCP-1 is substituted by alanine.

7. A pharmaceutical composition comprising the MCP-1 derivative of claim 1 and a pharmaceutically acceptable carrier.

8. A pharmaceutical composition comprising the MCP-1 derivative of claim 2 and a pharmaceutically acceptable carrier.

9. A pharmaceutical composition comprising the MCP-1 derivative of claim 3 and a pharmaceutically acceptable carrier.

10. A pharmaceutical composition comprising the MCP-1 derivative of claim 4 and a pharmaceutically acceptable carrier.

11. A pharmaceutical composition comprising the MCP-1 derivative of claim 5 and a pharmaceutically acceptable carrier.

12. A pharmaceutical composition comprising the MCP-1 derivative of claim 6 and a pharmaceutically acceptable carrier.

13. A method of treating restenosis by administering to a patient in need thereof the MCP-1 derivative of claim 1.

14. A method of treating restenosis by administering to a patient in need thereof the MCP-1 derivative of claim 2.

15. A method of treating restenosis by administering to a patient in need thereof the MCP-1 derivative of claim 3.

16. A method of treating restenosis by administering to a patient in need thereof the MCP-1 derivative of claim 4.

17. A method of treating restenosis by administering to a patient in need thereof the MCP-1 derivative of claim 5.

18. A method of treating restenosis by administering to a patient in need thereof an effective amount of the MCP-1 derivative of claim 6.

19. A method of inhibiting monocyte chemoattractant activity by administering to a patient in need of treatment thereof an effective amount of the MCP-1 derivative of claim 1.

20. A method of inhibiting monocyte chemoattractant activity by administering to a patient in need of treatment thereof an effective amount of the MCP-1 derivative of claim 2.

21. A method of inhibiting monocyte chemoattractant activity by administering to a patient in need of treatment thereof an effective amount of the MCP-1 derivative of claim 3.

22. A method of inhibiting monocyte chemoattractant activity by administering to a patient in need of treatment thereof an effective amount of the MCP-1 derivative of claim 4.

23. A method of inhibiting monocyte chemoattractant activity by administering to a patient in need of treatment thereof an effective amount of the MCP-1 derivative of claim 5.

24. A method of inhibiting monocyte chemoattractant activity by administering to a patient in need of treatment thereof an effective amount of the MCP-1 derivative of claim 6.

25. The human MCP-1 derivative of claim 1, wherein 24-arginine is substituted with another amino acid.

26. The human MCP-1 derivative of claim 25, wherein 3-aspartate is substituted with another amino acid.

27. A human Monocyte Chemoattractant Protein-1 (MCP-1) derivative wherein one or more of the 24-arginine, 3-aspartate and the 2–8 amino acid sequence have been deleted or substituted by one or more amino acids, the MCP-1 derivative being capable of inhibiting the monocyte chemoattractant activity of endogenous MCP-1.

* * * * *

UNITED STATES PATENT AND TRADEMARK OFFICE
CERTIFICATE OF CORRECTION

PATENT NO. : 5,459,128
DATED : October 17, 1995
INVENTOR(S) : Barrett Rollins and Yu Jun Zhang It is certified that error appears in the above-identified patent and that said Letters Patent is hereby corrected as shown below:

Column 6, line 29: delete "2-8-tyrosine" and insert therefor --28-tyrosine--;

Column 8, line 11: delete "claim 25" and insert therefor --claim 1--.

Signed and Sealed this

Nineteenth Day of March, 1996

Attest:

BRUCE LEHMAN

*Attesting Officer*     *Commissioner of Patents and Trademarks*